United States Patent [19]
Sato et al.

[11] Patent Number: 6,011,110
[45] Date of Patent: Jan. 4, 2000

[54] CARRIER FOR BIOREACTOR AND METHOD OF PRODUCING THE SAME

[75] Inventors: Takaya Sato; Tsutomu Uehara; Hiroshi Yoshida, all of Tokyo, Japan

[73] Assignee: Nisshinbo Industries, Inc., Japan

[21] Appl. No.: 08/915,717

[22] Filed: Aug. 21, 1997

[30] Foreign Application Priority Data

Sep. 13, 1996 [JP] Japan .................................. 8-263856

[51] Int. Cl.⁷ ...................................... C08J 3/03
[52] U.S. Cl. .................... 524/591; 424/409; 521/170; 521/174; 524/916
[58] Field of Search ................ 424/409; 524/591, 524/916; 521/170, 174

[56] References Cited

U.S. PATENT DOCUMENTS

| | | |
|---|---|---|
| 4,118,354 | 10/1978 | Harada et al. . |
| 4,160,076 | 7/1979 | Guthrie et al. ............... 521/159 |
| 4,209,605 | 6/1980 | Hoy et al. ..................... 528/54 |
| 4,816,509 | 3/1989 | Fukushima et al. ......... 524/413 |
| 4,920,172 | 4/1990 | Daoud .......................... 524/502 |
| 5,000,955 | 3/1991 | Gould et al. . |
| 5,104,909 | 4/1992 | Grasel et al. ................. 521/159 |
| 5,116,937 | 5/1992 | Greene ......................... 528/272 |
| 5,563,233 | 10/1996 | Reich et al. .................. 528/76 |
| 5,674,917 | 10/1997 | Wilson ........................ 521/109.1 |
| 5,719,201 | 2/1998 | Wilson ......................... 521/174 |
| 5,728,762 | 3/1998 | Reich et al. .................. 524/379 |
| 5,932,200 | 8/1999 | Reich et al. .................. 524/591 |

FOREIGN PATENT DOCUMENTS

| | | |
|---|---|---|
| 0 333 899 | 9/1989 | European Pat. Off. . |
| 0 465 131 | 1/1992 | European Pat. Off. . |
| WO95/15352 | 6/1995 | WIPO . |

OTHER PUBLICATIONS

*Patent Abstracts of Japan*, vol. 097, No. 006 (Abstract of JP 09–05179 ) (1997).
*Patent Abstracts of Japan*, vol. 011, No. 200 (C–431) (Abstract of JP 62–022591) (1987).

Primary Examiner—John M. Cooney, Jr.
Attorney, Agent, or Firm—Wenderoth, Lind & Ponack, L.L.P.

[57] ABSTRACT

A bioreactor carrier is provided which is a thermoplastic organic high molecular compound having a swelling rate of volume in water of 150–4,000% and which is useful as a carrier to which animal cells, plant cells, microorganisms and/or protozoans are fixed to obtain a bioreactor for substance production, harmful substance treatment, waste oil treatment, wastewater treatment, deodorization or the like. A method of producing the carrier includes the steps of reacting long-chain and short-chain polyol compounds and an isocyanate compound to obtain a thermoplastic resin, heating the thermoplastic resin to its melting temperature thereby plasticizing it, extruding the plasticized resin into strands with an extruder, and continuously chopping the strands into pellets.

7 Claims, 2 Drawing Sheets

CARRIER FOR BIOREACTOR AND METHOD OF PRODUCING THE SAME

BACKGROUND OF THE INVENTION

1. Field of the Invention

This invention relates to a thermoplastic water-absorptive gel carrier for use as a carrier to which animal cells, plant cells, microorganisms and/o:- protozoans are fixed to obtain a bioreactor for substance production, harmful substance treatment, waste oil treatment, wastewater treatment, deodorization and the like.

2. Description of the Background Art

The carriers used in bioreactors are of two types: porous and gel (nonporous). Porous carriers include those made of polyurethane, cellulose, polypropylene, polyvinyl formal and ceramic.

The porosity of these carriers gives them a large surface area. They are frequently used with animal cells, plant cells, microorganisms and/or protozoans fixed to their porous surfaces.

Porous carriers have various disadvantages, however. Polyurethane and polypropylene porous bodies are hydrophobic and therefore have poor fluidity in water. In addition, they resist adherence of animal cells, plant cells, microorganisms and protozoans. Cellulose porous bodies are susceptible to erosion by such organisms and are therefore short in service life. Among other shortcomings, polyvinyl formal porous bodies have the drawback that no method has been established for their production on an industrial scale. Ceramic porous bodies are restricted in method of use since their high specific gravity prevents them from being fluidized in water.

Gel carriers include those made of polyacrylamide, polyethylene glycol, polyvinyl alcohol and alginic acid.

Although these gel carriers are generally used with animal cells, plant cells, microorganisms and/or protozoans fixed by envelopment within the gel, they can also be used with animal cells, plant cells, microorganisms and/or protozoans fixed to the gel surface.

Since these gel carriers contain water to a high degree, they exhibit high biocompatibility and offer a favorable habitat for animal cells, plant cells, microorganisms, and protozoans except for polyacrylamide gel carrier prepared from acrylamide, which is cytotoxic. On the other hand, most of these gel carries are inferior in physical strength owing their high water content. They are therefore highly likely to experience wear and breakage during use in the reactor.

Gel carriers reported to date, including those mentioned above, fall in the categories heat cured, low-temperature cured, ion-crosslinking cured and radiation cured organic polymer compounds.

Once these carriers have been formed into a specific shape, they cannot be remelted and changed into another shape. They are therefore usually cut to the desired size.

The process of cutting the water-impregnated and swollen gel into several millimeter sized cubes is very laborious. The production of conventional gel carriers has therefore been extremely troublesome and involved long production time and high cost. In addition, high volume production of the gels is difficult. These factors are believed to account for the failure of gel carriers to achieve wide utilization in bioreactors.

An object of the invention is to provide a bioreactor carrier made of thermoplastic water-absorptive gel which contains a high degree of water, has excellent physical strength, exhibits strong resistance to erosion by organisms, and can be readily produced industrially in high volume.

SUMMARY OF THE INVENTION

For achieving this object, this invention provides a method of producing:

(1) a bioreactor carrier which is a thermoplastic organic polymer compound having a swelling rate of volume in water of 150–4,000%, (2) the bioreactor carrier of (1) wherein the thermoplastic organic polymer compound is a polyurethane water-absorptive gel obtained by reacting long-chain and short-chain polyol compounds and an isocyanate compound, (3) a carrier for wastewater treatment utilizing the bioreactor carrier of (1) or (2), (4) a carrier for deodorization utilizing the bioreactor carrier of (1) or (2), and (5) a method of producing a bioreactor carrier formed by reacting long-chain and short-chain polyol compounds and an isocyanate compound to obtain a thermoplastic resin, heating the thermoplastic resin to its melting temperature thereby plasticizing it, extruding the plasticized resin into strands with an extruder, and continuously chopping the strands into pellets.

When this bioreactor carrier made of thermoplastic water-absorptive gel is used, the stirring efficiency and the concentration of animal cells, plant cells, microorganisms and/ or protozoans in the reactor are enhanced, thereby enabling high treatment performance.

DETAILED DESCRIPTION OF THE PREFERRED EMBODIMENTS

The bioreactor carrier made of thermoplastic water-absorptive gel (hereinafter called "thermoplastic gel carrier") according to this invention is made of a material that has extremely high hydrophilicity and is able to retain a large amount of water therein. As such, it is highly compatible with animal cells, plant cells, microorganisms, and protozoans.

The thermoplastic gel carrier of this invention is cast into a culture solution containing animal cells, plant cells, microorganisms and/or protozoans for use. Owing to the high biocompatibility of the carrier material, the animal cells, plant cells, microorganisms and/or protozoans present in the solution adhere to the surfaces of the gel particles and proliferate thereon.

Unlike a spongy porous carrier, the invention thermoplastic gel carrier does not have a porous structure observable with the naked eye. Sticky animal cells, plant cells, microorganisms and protozoans, e.g., ammonium oxidizing bacteria, nitrite oxidizing bacteria, other bacteria for nitrification, denitrification bacteria and molds, therefore adhere preferentially to the thermoplastic gel carrier surfaces.

The culture solution or water for treatment containing the thermoplastic gel carrier is stirred by aeration stirring or agitator stirring. This causes the animal cells, plant cells, microorganisms and/or protozoans which exhibit low stickiness with the carrier to peel from and fall off the surfaces of thermoplastic gel carrier particles.

Only the sticky animal cells, plant cells, microorganisms and/or protozoans adhere to the thermoplastic gel carrier in large numbers to be fixed thereto. These microorganisms therefore resist separation during fluidization. An effect is consequently obtained whereby only those animal cells, plant cells, microorganisms and/or protozoans with high stickiness propagate on the carrier particle surfaces. This is a particularly notable feature of the invention thermoplastic gel carrier.

Unlike the conventional water-containing gel, the invention thermoplastic gel carrier is high in shearing resistance. The thermoplastic gel carrier particles with large numbers of animal cells, plant cells;, microorganisms and/or protozoans serving as a biological catalyst densely fixed to their outer surfaces can therefore withstand efficient stirring by use of an impeller agitator or the like.

As an example, an explanation will now be given regarding wastewater treatment, particularly regarding treatment for deamination (biological nitrification) which is the oxidization of ammonia state nitrogen into nitrate state nitrogen.

Figure 1:
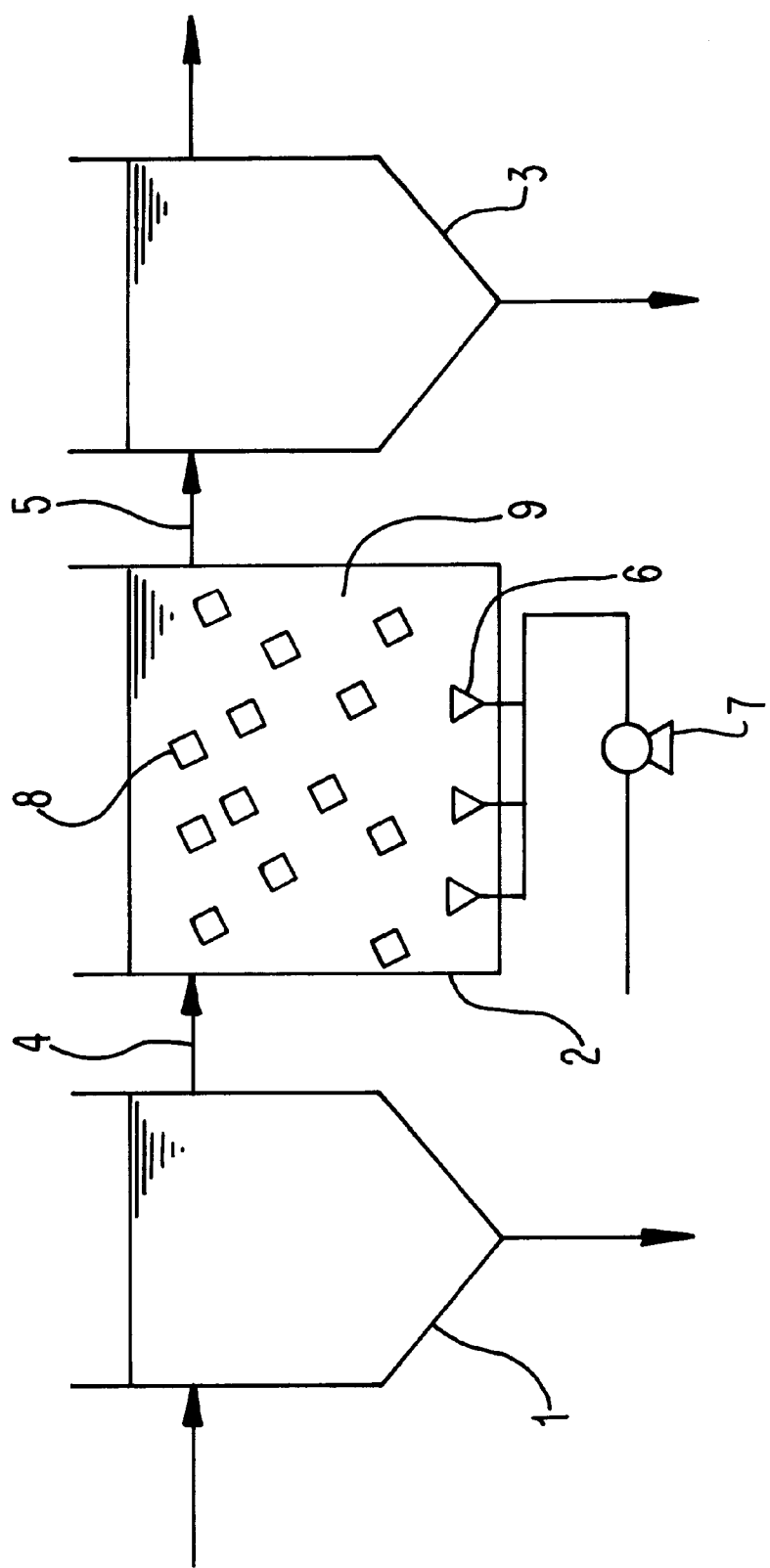
FIG. 1 is a schematic view for explaining an activated sludge method and a wastewater treatment system using the thermoplastic gel carrier of this invention.

FIG. 1 is a schematic view for explaining a wastewater treatment system using by an activated sludge method the thermoplastic gel carrier of this invention. In this figure, reference numeral 1 designates a pre-sedimentation basin, 2 a biological reactor and 3 a post-sedimentation basin. Wastewater 4 is supplied from the pre-sedimentation basin 1 to the biological reactor 2 and treated biologically therein. The treated water 5 is removed of sediment in the post-sedimentation basin 3 and the supernatant water is discharged.

The biological reactor 2 is equipped with diffusers 6 which supply oxygen or air adjusted to an appropriate oxygen concentration for aeration. The air containing oxygen is supplied to the diffusers 6 by a blower 7.

The thermoplastic gel carrier 8 of this invention is cast into the biological reactor 2. As wastewater 4 is being fed to the biological reactor 2 and treated water 5 is being forwarded to the post-sedimentation basin 3, oxygen-containing air is blown from the diffusers 6 to supply oxygen to the mixed liquor 9 in the biological reactor 2.

The convection produced in the mixed liquor 9 by the upward flow of bubbles occurring at this time causes the particles of thermoplastic gel carrier 8 to float and circulate within the biological reactor 2. The organisms which decompose and remove the organic pollutants present in the mixed liquor 9 attach and fixed to the thermoplastic gel carrier 8.

Since the thermoplastic gel carrier 8 has a very high water content at this time, it is highly compatible with the organisms. The mixed liquor 9 includes groups of floating organisms. These groups are of many types including, for example, BOD digest bacteria; oxidation bacteria of organic compounds that utilize organic pollutants as their nutrient source, nitrification bacteria that decompose ammonia state nitrogen into nitrate state nitrogen and denitrifying bacteria that convert nitrate state nitrogen into nitrogen gas.

Since these organism groups look like grains of mud in water, they are also collectively referred to as activated sludge. The activated sludge may also contain earthworms, rotifers, vorticellae and other protozoans.

Among these floating organism groups, those with high stickiness, e.g., the ammonium oxidizing bacteria, nitrite oxidizing bacteria, other bacteria for nitrification, denitrification bacteria and molds, positively fix themselves to the surfaces of the thermoplastic gel carrier particles. In the biological reactor 2, the organic pollutants and nitrogen components in the wastewater are decomposed and removed by the action of both the organism groups fixed to the surfaces of the carrier particles and the floating organism groups.

Since the ammonia state nitrogen contained in wastewater has been found to be a primary cause of river and ocean pollution, it is now seen as necessary to lower the amount of this pollutant in wastewater. The nitrification bacteria present in activated sludge convert the ammonia state nitrogen in wastewater to nitrate state nitrogen and the denitrifying bacteria therein convert the nitrate state nitrogen to nitrogen gas which is released into the atmosphere.

Since nitrification bacteria are very slow breeders, their concentration among the floating organism groups, i.e., in the activated sludge, is not very high. The activated sludge method used in ordinary wastewater treatment is therefore unable to treat ammonia state nitrogen adequately.

The inventors made a study to determine why nitrification bacteria do not multiply in activated sludge. They came to the following conclusion.

The total number of organisms present in a given unit volume can be considered to be substantially constant. When rapidly multiplying bacteria like oxidation bacteria of organic compounds are present in the activated sludge, therefore, only the BOD digest bacteria; oxidation bacteria of organic compounds proliferate and slow multiplying bacteria like bacteria for nitrification cannot easily multiply. The bacteria for nitrification concentration of the activated sludge is therefore always low. This can be avoided by breeding only the bacteria for nitrification at a separate place. Since bacteria for nitrification are sticky, they can adhere to the smooth surface of the thermoplastic gel carrier particles.

On the other hand, BOD digest bacteria; oxidation bacteria of organic compounds and other such bacteria with low stickiness cannot adhere to the surfaces of the carrier particles. In the vicinity of the carrier particles, therefore, only bacteria for nitrification multiply to a high concentration.

Use of the thermoplastic gel carrier of this invention amounts to separating the habitats of the bacteria for nitrification and the BOD digest bacteria; oxidation bacteria of organic compounds. The bacteria for nitrification which adhere to the thermoplastic gel carrier surfaces biologically treat the ammonia state nitrogen with excellent efficiency and high speed.

In contrast, when a porous carrier is used, sludge catches at the pore portions of the spongy carrier and the resulting rise in the sludge density in the biological reactor enhances the wastewater treatment performance. What the inventors refer to as the "habitat separation effect" is therefore small. Because of this, the porous carrier is generally inferior to the thermoplastic gel carrier in ammonia state nitrogen treatment performance.

The foregoing explanation focuses mainly on wastewater treatment for decomposing ammonia state nitrogen in the wastewater into nitrate state nitrogen. The invention thermoplastic gel carrier is not limited to this application, however, and can also be used in other wastewater processing steps such as denitrification and in biocatalytic reactions for other than wastewater treatment.

Although this invention does not particularly limit the size or shape of the thermoplastic gel carrier particles, particles of cubical, cylindrical, spherical and other shapes providing large surface area are preferable. Chip-like particles of uniform size can also be used.

Cubical particles measuring 1–8 mm per side, cylindrical particles measuring 5 mm in diameter and 5 mm in length, and spherical particles measuring 5 mm in diameter can be mentioned as preferable examples.

The thermoplastic gel carrier particles can uniformly fluidize in the reactor when their specific gravity is 1.000–1.250 after the adherence and fixing of the organisms reaches a steady state. It is therefore preferable to adjust the specific gravity of the thermoplastic gel carrier to fall in this range. Adjustment of specific gravity is effected by addition of a high specific gravity powder such as barium sulfate during the thermoplastic resin synthesis before forming or when the resin is in a molten state during hot-forming. An inorganic powder such as activated carbon, carbon powder, zeolite or the like can be incorporated into the thermoplastic gel carrier to ensure adherence of a large amount of desired animal cells, plant cells or microorganisms. The addition can be made when the resin is in a molten state, similarly to the case of adding the aforesaid high-specific-gravity powder. Otherwise, it can be effected by adhering the inorganic powder to the surface of thermoplastic resin strands extruded from an extruder prior to chopping the strands.

The invention thermoplastic gel carrier before water swelling plasticizes and exhibits fluidity when heated to its melting temperature. It can be formed into pellets by extruding it in strands from an extruder with heating capability and then continuously chopping the strands into segments of appropriate length. When the thermoplastic resin is to be formed into carrier chips, it is crushed and then sifted for separation into chips of uniform size. Most commonly used bioreactor carriers are made of thermosetting polymer resins. Since such a resin has to be cut many times to obtain particles of desired shape, the operation is extremely troublesome. In contrast, the carrier according to this invention is made of thermoplastic resin which can be plasticized by heating. It is therefore highly advantageous in that it enables formation of carrier particles of desired shape and permits ready production of carrier particles of regular shape and size.

Nearly spherical carrier particles can be produced by chopping the aforesaid strands with an underwater pelletizer or similar apparatus. Injection molding is of course also possible and enables carrier particles of plate, block, wavy and various other shapes to be formed as desired by using different dies. The thermoplastic gel carrier of such shapes can, after swelling, be allowed to sink to the bottom of a biological reactor for use as a fixed bed. The thermoplastic gel carrier of this invention does not contain water at the time of forming.

At the time of use, the thermoplastic gel carrier are cast into the reactor where they swell by absorbing water therein. Since the carrier does not contain animal cells, plant cells, microorganisms or protozoans, it can be stored for long periods in a moistureproof bag.

Conventional gel carriers made of polyacrylamide, polyethylene glycol, polyvinyl alcohol, alginic acid and the like contain water and animal cells, plant cells, microorganisms and/or protozoans therein. Their storage therefore has to be carefully managed to keep the animal cells, plant cells, microorganisms and/or protozoans alive.

In addition, their high water content makes them very expensive to transport to the site of use in large quantities. As the thermoplastic gel carrier of this invention can be transported as a dry material and used after absorbing water in the reactor, it can be transported at markedly lower cost. Since the carrier can be adhered with large numbers of desired animal cells, plant cells, and/or other organisms by effecting the water absorption in a suspension containing the desired animal cells, plant cells, and/or other organisms at high concentration, the initial performance of the bioreactor can be enhanced.

Unlike the conventional water-containing gel, the invention thermoplastic gel carrier is very high in shearing resistance. The carrier with large numbers of animal cells, plant cells, microorganisms and/or protozoans fixed to its outer surfaces can therefore withstand efficient stirring by use of an impeller agitator or the like. Aeration stirring by use of air or other gas is used for stirring the carrier in an aerobic biological reactor. An impeller agitator or the like must be used for the stirring in an anaerobic or anoxic biological reactor, however, since use of aeration stirring is not permissible. Under such stirring, the thermosetting carrier three-dimensionally crosslinked to a high degree is disintegrated by the stirring because its low shearing resistance makes it fragile. The thermoplastic gel carrier of this invention preferably has a swelling rate of volume in water defined by Equation 1 falling in the range of 150–4,000%.

$$\text{Swelling rate of volume } (\%) = \frac{\text{Completely swollen volume in water } (\text{cm}^3)}{\text{Dry volume. } (\text{cm}^3)} \times 100 \quad \text{Equation 1}$$

By "dry volume" is meant the state of the thermoplastic gel carrier when its weight loss becomes minimal during drying at 100° C. By "completely swollen volume" is meant the state thereof when the change in its volume becomes minimal during soaking in 25° C. pure water. The volume of rectangular or cubical carrier particles is determined from the length of the sides. In the case of cylindrical pellets and chips formed by crushing, whose volumes are hard to determine by calculation, the following method is used to obtain the dry and completely swollen volumes.

Dry volume: Calculated from specific gravity of thermoplastic resin before hot-forming or before crushing and pellet or chip weight after 100° C. drying.

Completely swollen volume: An appropriate amount of completely swollen pellets or chips are placed in a measuring flask equipped with an airtight stopper, the flask is filled to a marked line with pure water, the pellets or chips are left to stand in the water at 4° C. for 1 hr, and the total weight is measured as A(g).

The pellets or chips are removed from the flask and the weight of the measuring flask and the pure water remaining in the flask is measured as B(g).

The measured values are substituted into the equation:

Completely swollen volume (ml)=(A−B)×1.00

When the swelling rate of volume is less than 150%, the water absorptivity of the thermoplastic gel carrier is low. Its water content is therefore so small as to make the description "water-containing gel" inappropriate. The adherence of organisms is therefore poor. When the swelling rate is greater than 4,000%, the thermoplastic gel carrier falls so low in strength as to lose its utility.

Gels usable for the thermoplastic gel carrier of the invention include, for example, thermoplastic polyethylene glycol gel, thermoplastic polyurethane gel and the like. The thermoplastic polyurethane gel carrier is a polyurethane copolymer consisting of soft segments and hard segments randomly bonded head to tail by urethane bonding. It is synthesized by reacting a bifunctional long-chain diol compound, a bifunctional diisocyanate compound and a short-chain diol compound. The soft segment obtained by reacting the long-chain diol compound and the isocyanate compound is represented by the Formula 2:

Formula 2
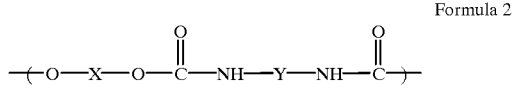

The hard segment obtained by reacting the short-chain diol compound and the isocyanate compound is represented by the Formula 3:

Formula 3
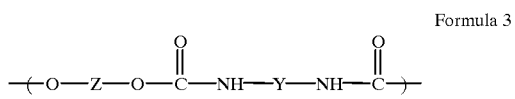

The symbol X in Formula 2 represents a group produced by reaction of a terminal hydroxy group of a long-chain diol compound with an isocyanate, less the terminal hydroxy group thereof. The molecular weight of X is thought to greatly affect the swelling rate and the like of the gel. Its molecular weight is preferably between 1,000 and 13,000, more preferably between 4,000 and 8,000. When the molecular weight of X is small, the molecular weight of the soft segment becomes small. Since the swelling rate of the gel therefore tends to be low, the specific gravity in water of the gel increases. When the molecular weight of X is larger than 13,000, the viscosity rises during synthesis. This is disadvantageous since it increases the melting temperature and causes other problems.

The long-chain diol compound used in this invention is preferably a water-soluble polyoxyalkylenediol (polyol), most preferably a water-soluble ethylene oxide-propylene oxide copolymer having two terminal hydroxy groups per molecule, or polyethylene glycol.

The ethylene oxide content is preferably 70% or greater, more preferably 85% or greater. At an ethylene oxide content of less than 70%, the swelling rate of the gel may be low.

The symbol Y in the formulas represents a group produced by reaction of a diisocyanate compound having a number-average molecular weight between 100 and 1,000 with a hydroxide group, less the isocyanate group.

Isocyanates usable in the invention include, for example, tolylene diisocyanate, xylylene diisocyanate, naphthylene diisocyanate, diphenylmethane diisocyanate, biphenylene diisocyanate, diphenylether diisocyanate, tolidine diisocyanate, hexamethylyne diisocyanate and isophoron diisocyanate.

The symbol Z in Formula 3 represents a group produced by reaction of a terminal hydroxide of a low molecular diol having a number-average molecular weight between 30 and 400 with an isocyanate, less the terminal hydroxy group thereof.

Short-chain diol compounds usable in the invention include, for example, ethylene glycol, 1,2-propylene glycol, 1,3-propylene glycol, 1,3-butanediol, 2,3-butanediol, 1,4-butanediol, 1,5-pentanediol, 1,6-hexanediol, 2,2-dimethyl-1,3-propanediol, diethylene glycol, dipropylene glycol, 1,4-cyclohexanedimethanol, 1,4-bis-(β-hydroxyethoxy)benzene, p-xylylenediol, phenyldiethanolamine, methyldiethanolamine and 3,9-bis-(2-hydroxy-1,1-dimethylethyl)-2,4,8,10-tetraoxaspiro[5,5]-undecane.

The ratio between the contents of the long-chain diol compound and the short-chain diol compound used in the invention can be varied depending on the molecular weights of the compounds, the physical properties of the gel desired, and the like. Although the preferable mole ratio between the long-chain diol compound and the short-chain dial compound varies depending on the molecular weight of the long-chain diol compound, it is generally in the range of 5:1 to 1:2. When a long-chain dial compound of high molecular weight is used, the mole ratio of the short-chain diol compound for forming the hard segment is preferable made small because such a long-chain dial compound tends to raise the viscosity during thermoplastic resin synthesis. On the other hand, when it is desired to increase the swelling rate of volume while maintaining high physical strength, the mole ratio of the short-chain dial compound is preferably increased. The number of isocyanate groups of the diisocyanate compound relative to the total number of hydroxy groups of the two compounds (NCO/OH) is preferably in the range of 0.95–1.8, more preferably in the range of 1.0–1.6. Thus this invention not only permits use of polyurethane copolymers having undergone thorough polymer synthesis reaction but also permits use of incomplete thermoplastic polyurethanes, i.e., permits polyurethane copolymers having remaining active groups such as isocyanate groups to be used by subjecting them to crosslinking after formation.

The thermoplastic polyurethane gel used in this invention can be synthesized either by the prepolymer method of reacting the long-chain diol compound and the diisocyanate compound first and then reacting the result with the short-chain diol compound as a chain extender or the one-shot method of mixing all of the reaction materials at one time.

Although the method of producing thermoplastic polyurethane gels explained in the foregoing is typical, the invention is not limited to use of gels produced by this method but can also use thermoplastic water-absorptive gels produced by other methods insofar as they are thermoplastic resins satisfying the condition of a swelling rate of volume in water of 150–4,000%.

EXAMPLES

The invention will now be explained with reference to specific examples. It is not, however, limited to the described examples.

Example 1
(Production of Thermoplastic Polyurethane Gel)

One hundred parts by weight of polyethylene glycol having an average molecular weight of 2,000 used as the long-chain diol compound was placed in a reactor equipped with a stirrer. Preheating was conducted at 110° C. for 1 hour under a nitrogen gas atmosphere to drive off the water content of the polyethylene glycol. The temperature in the reactor was then set to 130° C. Twenty-five parts by weight of 4,4' diphenylmethane diisocyanate was added to the reactor as the polyisocyanate compound and reaction was effected for two hours with stirring. Upon completion of the prepolymer reaction, 1.19 parts by weight of 1,4-butanediol was added to the reactor as a chain extender and stirring was conducted for 1 hour. All reactions after preheating were conducted at 130° C. Upon completion of the reaction, the product was spread by pouring it onto a vat treated with a release agent and heat treated at 100° C. for 4 hours to obtain a thermoplastic polyurethane resin composition. The thermoplastic polyurethane resin composition produced in this manner was cooled and then crushed into fine particles. The particles were supplied to a heating extruder and melted by heating to 180–230° C. under application of shearing force. The 3-mm diameter strands extruded from the nozzle were chopped into 3-mm long pellets to obtain cylindrical resin pellets. The pellets were swollen with water to obtain thermoplastic gel carrier pellets. The swelling rate of volume of the thermoplastic gel carrier in water was 450%.

Example 2
(Production of Thermoplastic Polyurethane Gel)

Thermoplastic gel carrier pellets were obtained in the same manner as in Example 1 except that 100 parts by weight of polyethylene glycol having an average molecular weight of 6,000 was used as the long-chain diol compound, 8.3 parts by weight of 4,4' diphenylmethane diisocyanate was used as the polyisocyanate compound, and 0.4 part by weight of 1,4-butanediol was used as the chain extender. The swelling rate of volume of the thermoplastic gel carrier in water was 1,600%.

Example 3
(Production of Thermoplastic Polyurethane Gel)

Thermoplastic gel carrier pellets were obtained in the same manner as in Example 1 except that 100 parts by weight of polyethylene glycol having an average molecular weight of 10,000 was used as the long-chain diol compound, 5.0 parts by weight of 4,4' diphenylmethane diisocyanate was used as the polyisocyanate compound, and 0.24 part by weight of 1,4-butanediol was used as the chain extender. The swelling rate of volume of the thermoplastic gel carrier in water was 2,600%.

Example 4
(Production of Thermoplastic Polyurethane Gel)

Thermoplastic gel carrier pellets were obtained in the same manner as in Example 1 except that 100 parts by weight of polyethylene glycol having an average molecular weight of 6,000 was used as the long-chain diol compound, 8.3 parts by weight of 4,4' diphenylmethane diisocyanate was used as the polyisocyanate compound, and 1.53 parts by weight of 1,4-butanediol was used as the chain extender. The swelling rate of volume of the thermoplastic gel carrier in water was 1,400%.

Example 5
(Production of Thermoplastic Polyurethane Gel)

Thermoplastic gel carrier pellets were obtained in the same manner as in Example 1 except that 100 parts by weight of polyethylene glycol having an average molecular weight of 6,000 was used as the long-chain diol compound, 8.3 parts by weight of 4,4' diphenylmethane diisocyanate was used as the polyisocyanate compound, and 0.16 part by weight of 1,4-butanediol was used as the chain extender. The swelling rate of volume of the thermoplastic gel carrier in water was 2,000%.

Example 6
(Production of Thermoplastic Polyurethane Gel)

Thermoplastic gel carrier pellets were obtained in the same manner as in Example 1 except that 100 parts by weight of polyetherdiol (EO/PO=7/3) having an average molecular weight of 6,000 was used as the long-chain diol compound, 8.3 parts by weight of 4,4' diphenylmethane diisocyanate was used as the polyisocyanate compound, and 0.4 part by weight of 1,4-butanediol was used as the chain extender. The swelling rate of volume of the thermoplastic gel carrier in water was 400%.

Example 7
(Production of Thermoplastic Polyurethane Gel)

A thermoplastic polyurethane resin composition was obtained in the same manner as in Example 1 except that 100 parts by weight of polyethylene glycol having an average molecular weight of 6,000 used as the long-chain diol compound, 8.3 parts by weight of 4,4' diphenylmethane diisocyanate was used as the polyisocyanal:e compound, and 0.4 part by weight of 1,4-butanediol was used as the chain extender. The thermoplastic polyurethane resin composition was cooled and then crushed into fine particles. The particles were supplied to a heating extruder and melted by heating to 180–230° C. while being applied with shearing force to extrude the resin composition from the extruder nozzle. Activated carbon was applied to the surfaces of the extruded 3-mm diameter strands while they were still in a molten state. The strands were then cooled and chopped into 3-mm long segments to obtain cylindrical resin pellets. The pellets were swollen with water to obtain thermoplastic gel carrier pellets. The swelling rate of volume of the thermoplastic gel carrier in water was 1,600%.

Comparative Example 1
(Production of Thermoplastic Polyurethane Gel)

Thermoplastic gel carrier pellets were obtained in the same manner as in Example 1 except that 100 parts by weight of polyetherdiol (EO/PO=5/5) having an average molecular weight of 6,000 was used as the long-chain diol compound, 8.3 parts by weight of 4,4' diphenylmethane diisocyanate was used as the polyisocyanate compound, and 0.4 part by weight of 1,4-butanediol was used as the chain extender. The swelling rate of volume of the thermoplastic gel carrier in water was 120%.

Comparative Example 2
(Production of Thermoplastic Polyurethane Gel)

Thermoplastic gel carrier pellets were obtained in the same manner as in Example 1 except that 100 parts by weight of polyethylene glycol having an average molecular weight of 6,000 was used as the long-chain diol compound, 10.6 parts by weight of 4,4' diphenylmethane diisocyanate was used as the polyisocyanate compound, and 0.4 part by weight of 1,4-butanediol was used as the chain extender. The swelling of the carrier pellets when immersed in water was accompanied by foaming.

Comparative Example 3
(Production of Ion-Crosslinking Curable Polyvinyl Alcohol Gel)

Polyvinyl alcohol powder (polymerization degree: 2,000, saponification degree: 99.8%) was dissolved in water to prepare a 12 wt % aqueous solution of polyvinyl alcohol. With 500 g of this solution was mixed 250 g of a 4 wt % aqueous solution of sodium alginate. The mixed solution was added with 250 g of slurry obtained by concentrating activated sludge from an activated sludge wastewater treatment facility at the Tokyo Factory of Nisshinbo Industries, Inc. (sludge concentration: 1,500 mg/l) to a sludge concentration of 8,000 mg/l. The result was mixed to uniformity and dripped from a nozzle into a coagulating solution. The coagulating solution was an aqueous solution of boric acid at a concentration of 12 g/l and potassium chloride at a concentration of 30 g/l. The dripped liquor coagulated into spheres. The resulting gel spheres were removed and transferred to a saturated aqueous solution of sodium sulfate and left to stand therein for two hours. The polyvinyl alcohol carrier spheres obtained measured 4 mm in diameter.

Comparative Example 4
(Production of Crosslinked Polyethylene Glycol Carrier)

Fifteen parts by weight of non-thermoplastic three-dimensionally crosslinked polyethyleneglycol dimethacrylate (23G, Shin Nakamura Chemical Industries, Ltd.) and 0.6 part by weight of (dimethylamino)propionitrile were dissolved in 84.4 parts by weight of water. The solution was added with 35 parts by weight of a 0.2% aqueous solution of potassium persulfate, thoroughly stirred, poured into a mold and gelled. The gel was removed from the mold and cut to afford a polyethylene glycol carrier.

The compositions and swelling rates of volume of the gel carriers obtained in the foregoing Examples and Comparative Examples are shown in Table 1.

TABLE 1

| | Polyol | | MDI | 1,4 BDO | | Swelling rate of |
| --- | --- | --- | --- | --- | --- | --- |
| | Molecular weight | EO/PO ratio | Parts by weight/mole | Parts by weight/mole | Parts by weight/mole | NCO/OH ratio | volume (%) |
| Example 1 | 2,000 | 10/0 | 100/1 | 25/2 | 1.19/0.25 | 1.6 | 450 |
| Example 2 | 6,000 | 10/0 | 100/1 | 8.3/2 | 0.4/0.25 | 1.6 | 1,600 |
| Example 3 | 10,000 | 10/0 | 100/1 | 5.0/2 | 0.24/0.25 | 1.6 | 2,600 |
| Example 4 | 6,000 | 10/0 | 100/1 | 8.3/2 | 1.53/1 | 1.0 | 1,400 |
| Example 5 | 6,000 | 10/0 | 100/1 | 8.3/2 | 0.16/0.1 | 1.8 | 2,000 |
| Example 6 | 6,000 | 7/3 | 100/1 | 8.3/2 | 0.4/0.25 | 1.6 | 400 |
| Example 7 | 6,000 | 10/0 | 100/1 | 8.3/2 | 0.4/0.25 | 1.6 | 1,600 |
| Comparative Example 1 | 6,000 | 5/5 | 100/1 | 8.3/2 | 0.4/0.25 | 1.6 | 120 |
| Comparative Example 2 | 6,000 | 10/0 | 100/1 | 10.6/2.5 | 0.4/0.25 | 2.0 | Foamed |
| Comparative Example 3 | Ion-crosslinking curable polyvinyl alcohol gel | | | | | | — |
| Comparative Example 4 | Crosslinked polyethylene glycol carrier | | | | | | — |

TABLE 2

| | Abrasion survival rate (%) | Wastewater treatment test removal rate (%) |
| --- | --- | --- |
| Example 1 | 90 | — |
| Example 2 | 90 | 74 |
| Example 3 | 80 | — |
| Comparative Example 3 | ≦10 | 78 |
| Comparative Example 4 | ≦2 | 70 |

Example 8

The gel carriers obtained in Examples 1, 2 and 3 and Comparative Examples 3 and 4 were evaluated as set out below. The results are shown in Table 2.

(1) A container was prepared by gluing water-resistant sandpaper (#100) on the inner surface of a glass bottle for comparing carrier abrasion strength (diameter: 40 mm, length: 200 mm). The container was charged with 4-mm carrier cubes (30 ml as measured using a 100-ml measuring cylinder) and 120 ml water. After being stopped, the container was shaken at a reciprocation stroke of 70 mm and a rotational speed of 150 rpm for 20 hours. The contents were then removed and passed through a 1-mm screen. The volume of the carrier remaining on the screen was measured using the 100-ml measuring cylinder.

Abrasion survival rate (%)=(Apparent volume of carrier remaining on screen after test (ml)/30 ml)×100

Although the gel carrier of Example 2 exhibited about the same wastewater treatment removal rate as that of Comparative Examples 3 and 4, it was superior in abrasion survival rate.

Example 9

The gel carriers of Example 2 and Comparative Examples 3 and 4 were subjected to short-term wastewater treatment nitrification tests.

The wastewater treatment testing system of FIG. 1 was used. The 20-l aerator (biological reactor) 2 was charged with 2 l of carrier and 5 g·SS (active sludge) of nitrification column sludge. Tests were conducted using the artificial wastewater of Table 3 under the conditions of Table 4. One month after adding the carrier the system was assumed to have acclimatized and measurement of the ammonia state nitrogen of the raw water and the treated water was commenced. The average ammonia state nitrogen removal rate between the 30th and 100th day after carrier addition was determined. The results are shown in Table 1.

TABLE 3

| | Concentration (mg/l) |
| --- | --- |
| $NH_4Cl$ | 191.5 |
| $Na_2HPO_4 \cdot 12H_2O$ | 31.3 |
| $MgSO_4 \cdot 7H_2O$ | 4.3 |
| $CaCl_2 \cdot 2H_2O$ | 3.3 |
| KCl | 2.7 |
| $NH_4$-N | 50 |

TABLE 4

| | |
|---|---|
| HRT | 4–8 hrs |
| $NH_4$-N load | 0.15–0.30 kg · $N/m^3$ · day |
| Water temp. | 15–25° C. |
| pH | 6.0–7.0 |
| DO | 4.0–7.0 mg/l |

Example 10

Figure 2:
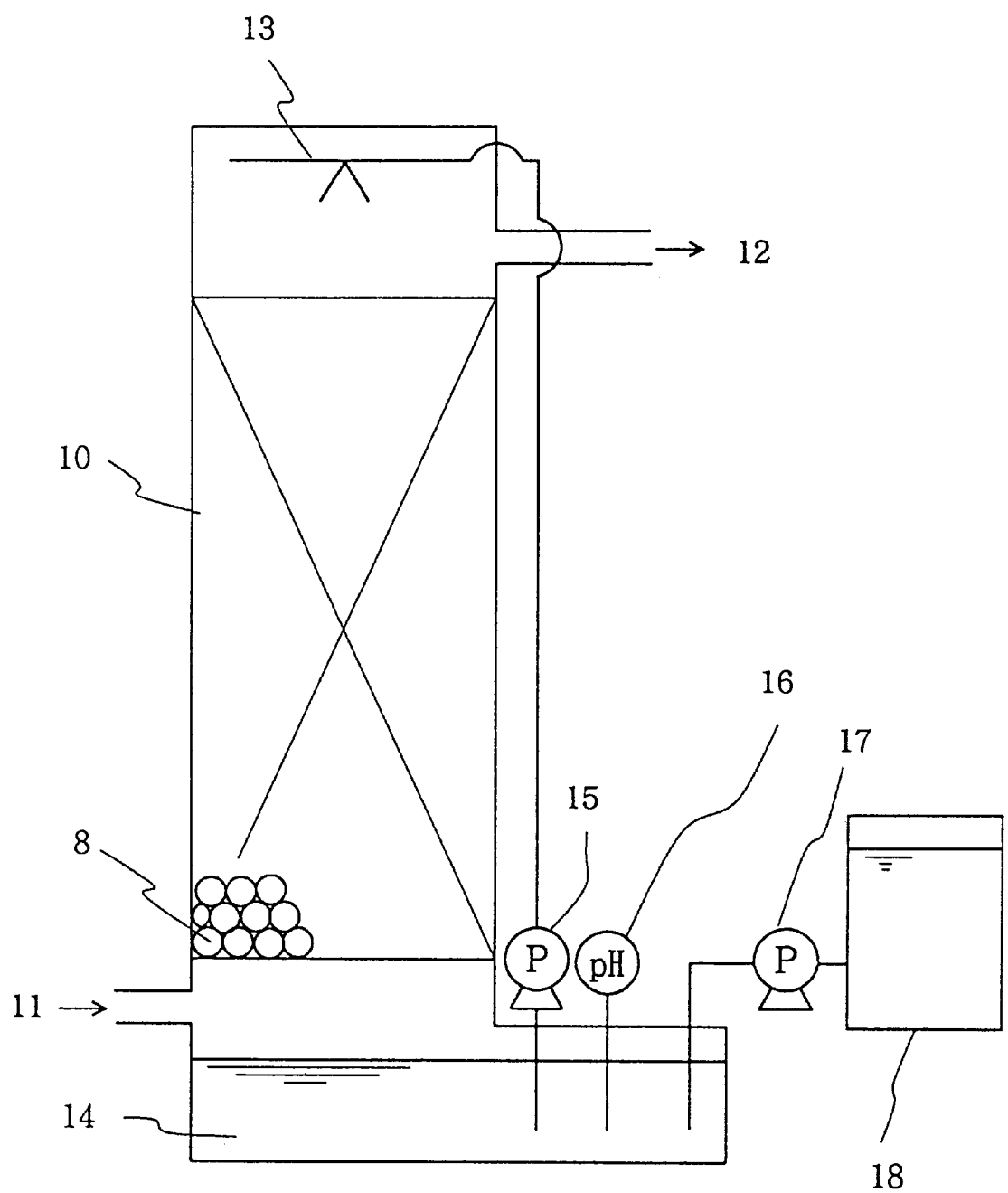
FIG. 2 is a schematic view of a system used to compare test gas deodorization performance by use of the thermoplastic gel carrier of this invention and peat moss.

The deodorization column 10 inside diameter: 100 mm, height: 600 mm) of the test system of FIG. 2 was charged with 4 l of gel carrier 8 obtained in Example 7. While sludge suspension from an adjustment tank 14 was being sprayed into the column 10 from a sprayer 13, air containing $NH_3$ was supplied through an inlet 11. The ammonia gas concentrations of at the inlet 11 and an outlet 12 were measured. For comparison, a test was similarly conducted with the column 10 charged with peat moss. The results of the tests are shown in Table 5.

In FIG. 2, 15 is a spray pump, 16 is a pH meter, 17 is a NaOH pump and 18 is a NaOH tank.

TABLE 5

| Charged carrier | | Example 7 gel carrier | Peat moss |
|---|---|---|---|
| Space velocity SV | l/hr · column | 240 | 240 |
| $NH_3$ concentration in | ppm | 5.2 | 5.0 |
| $NH_3$ concentration out | ppm | 1.1 | 2.3 |
| Ventilation resistance | mmAq/m | 19 | 52 |

As is clear from the forgoing Examples, the thermoplastic gel carrier of the invention is applicable to wastewater treatment, specifically treatment for decomposing ammonia state nitrogen contained in wastewater into nitrate state nitrogen, and to biological deodorization, specifically decomposition of ammonia gas. The thermoplastic gel carrier of the invention is not limited to these examples, however, and can also be advantageously applied to other wastewater treatment denitriding processes and the like and to other biocatalytic reactions for biological deodorization and the like.

The thermoplastic gel carrier of this invention exhibits excellent abrasion strength despite its high water content, exhibits hydrophilicity enabling animal cells, plant cells, microorganisms and/or protozoans to adhere thereto without impairing their physiological activities, and exhibits strong resistance to erosion by organisms.

Since the gel carrier readily adsorbs nitrification bacteria, it can treat ammonia state nitrogen efficiently and at high speed. The carrier can also tolerate long-periods of storage prior to use. Moreover, its exceptional shearing strength enables it to be efficiently stirred in a reactor.

What is claimed is:

1. A bioreactor carrier which is a thermoplastic organic polymer having a swelling rate of volume in water of 150 to 4,000%, wherein the thermoplastic organic polymer is a polyurethane water-absorptive gel obtained by reacting long-chain and short-chain diols and an isocyanate compound, said long-chain diol being a water-soluble ethylene oxide-propylene oxide copolymer having two terminal hydroxy groups per molecule, or polyethylene glycol with an ethylene oxide content of 70% or greater, said long-chain diol having a number-average molecular weight between 1,000 and 13,000, said short-chain diol having two terminal hydroxy groups per molecule and a number-average molecular weight between 30 and 400 and the reaction mole ratio of NCO/OH being in the range of 0.95–1.8.

2. A method of producing a bioreactor carrier comprising the steps of reacting long-chain and short-chain polyols and an isocyanate compound to obtain a thermoplastic resin, said long-chain diol being a water-soluble ethylene oxide-propylene oxide copolymer having two terminal hydroxy groups per molecule, or polyethylene glycol with an ethylene oxide content of 70% or greater, said long-chain diol having a number-average molecular weight between 1,000 and 13,000, said short-chain diol having two terminal hydroxy groups per molecule and a number-average molecular weight between 30 and 400 and the reaction mole ratio of NCO/OH being in the range of 0.95–1.8, heating the thermoplastic resin to its melting temperature thereby plasticizing it, extruding the plasticized resin into strands with an extruder, and continuously cutting the strands into pellets.

3. A carrier for waste water treatment utilizing the bioreactor carrier of claim 1.

4. A carrier for deodorization utilizing the bioreactor carrier of claim 1.

5. The bioreactor carrier according to claim 1, wherein said long-chain diol has a number-average molecular weight of from 4000 to 8000.

6. The method according to claim 2, wherein said long-chain diol has a number-average molecular weight of from 4000 to 8000.

7. The bioreactor carrier according to claim 1 which consists essentially of said thermoplastic organic polymer.

* * * * *